United States Patent [19]

Cooper et al.

[11] 4,416,281
[45] Nov. 22, 1983

[54] SURGICAL CUSHION FOR COOLING AN ORGAN

[75] Inventors: Albert A. Cooper, Abbott's Langley, England; Mohamed El-Rayes, Tripoli, Libya; Alan K. Yates, Warlingham, England

[73] Assignee: Guardline Disposables Limited, Hertfordshire, England

[21] Appl. No.: 267,428

[22] Filed: May 26, 1981

[30] Foreign Application Priority Data

Mar. 5, 1981 [GB] United Kingdom ............... 8106908

[51] Int. Cl.³ ............................................. A61F 7/00
[52] U.S. Cl. .................................... 128/400; 128/402
[58] Field of Search ............... 128/399, 400, 401, 402, 128/403, 39, 64, 65, 276, 132 D

[56] References Cited

U.S. PATENT DOCUMENTS

| 3,091,242 | 5/1963 | Johnson et al. | 129/402 |
| 3,496,932 | 2/1970 | Prisk et al. | 128/64 |
| 3,610,238 | 10/1971 | Rich, Jr. | 128/132 D |
| 3,625,221 | 12/1971 | Corbett | 128/276 |
| 3,717,199 | 2/1973 | Dienst | 128/401 |
| 3,763,857 | 10/1973 | Schrading | 128/132 D |
| 3,983,863 | 10/1976 | Janke et al. | 128/303 R |
| 4,217,890 | 8/1980 | Owens | 128/303 R |

Primary Examiner—C. Fred Rosenbaum
Assistant Examiner—C. W. Shedd
Attorney, Agent, or Firm—Berman, Aisenberg & Platt

[57] ABSTRACT

A cushion for cooling an organ of the body during surgery. The cushion is flexible and of open form to allow cooling fluid to flow into it and out of it. A flexible tube extends from the cushion for draining off cooling fluid from the cushion and regions adjacent thereto.

8 Claims, 6 Drawing Figures

SURGICAL CUSHION FOR COOLING AN ORGAN

The present invention relates to a cushion for use in cooling an organ of the body during surgery, especially during heart operations performed with the aid of local hypothermic ischaemic arrest.

In complex operations on the heart, it is desirable to arrest the heart to facilitate precise cardiac manipulation. To this end, the patient is linked to a cardio-pulmonary machine to allow circulation of the blood to bypass the heart. It has been found that operations of this kind lasting more than about 30 minutes, with no cooling of the heart tissue, result in an irreversible intracellular myocardial enzyme system decay.

Some difficult operations on the heart require cardiac arrest for longer than 30 minutes, however, and to increase the "safe" time within which there is no significant functional myocardial damage, surgeons have used local hypothermia, or cold cardioplegia, to reduce the metabolic rate of the heart. An example of the technique is described on page 48 of YATES A. K. (1976) Surgery of the Heart (edited by DYDE J. A. and SMITH R. E., Plenum Medical Books). A cold saline solution is flushed over and around the heart, a desired level of the solution being maintained by means of a room sucker. In order to ensure that the cold solution circulates over the posterior surface of the ventricular mass, the latter needs to be held clear of the posterior pericardium. If this is not done a "hot spot" will result where the heart takes up heat from the aorta even with the use of cold saline solution or slush and cardioplegic agents. This increases the risk of myocardial damage in that area.

To overcome these problems, a rigid double-plate platform is sometimes inserted behind the heart in order to space apart the heart and the aorta. This platform has one flat plate made of perforated metal, and another plate spaced therefrom by rigid members to which the metal plate is screwed. However, this double-plate platform has been found too cumbersome and too rigid for general use in heart operations.

It is an aim of the present invention to provide a less cumbersome aid for circulating cooling fluid around the heart or other organ of the body whilst reducing the risk of a "hot spot". Accordingly, the present invention is directed to a cushion for use in cooling an organ of the body during surgery, which cushion is flexible and is filamentous, porous, foamy, spongy, hollow or otherwise of open form or structure to allow cooling fluid to flow into it and out of it, and from which cushion extends a flexible tube for drawing off cooling fluid from the cushion or regions adjacent thereto.

An example of a surgical cushion in accordance with the present invention is illustrated in the accompanying drawings, in which.

Figure 1:
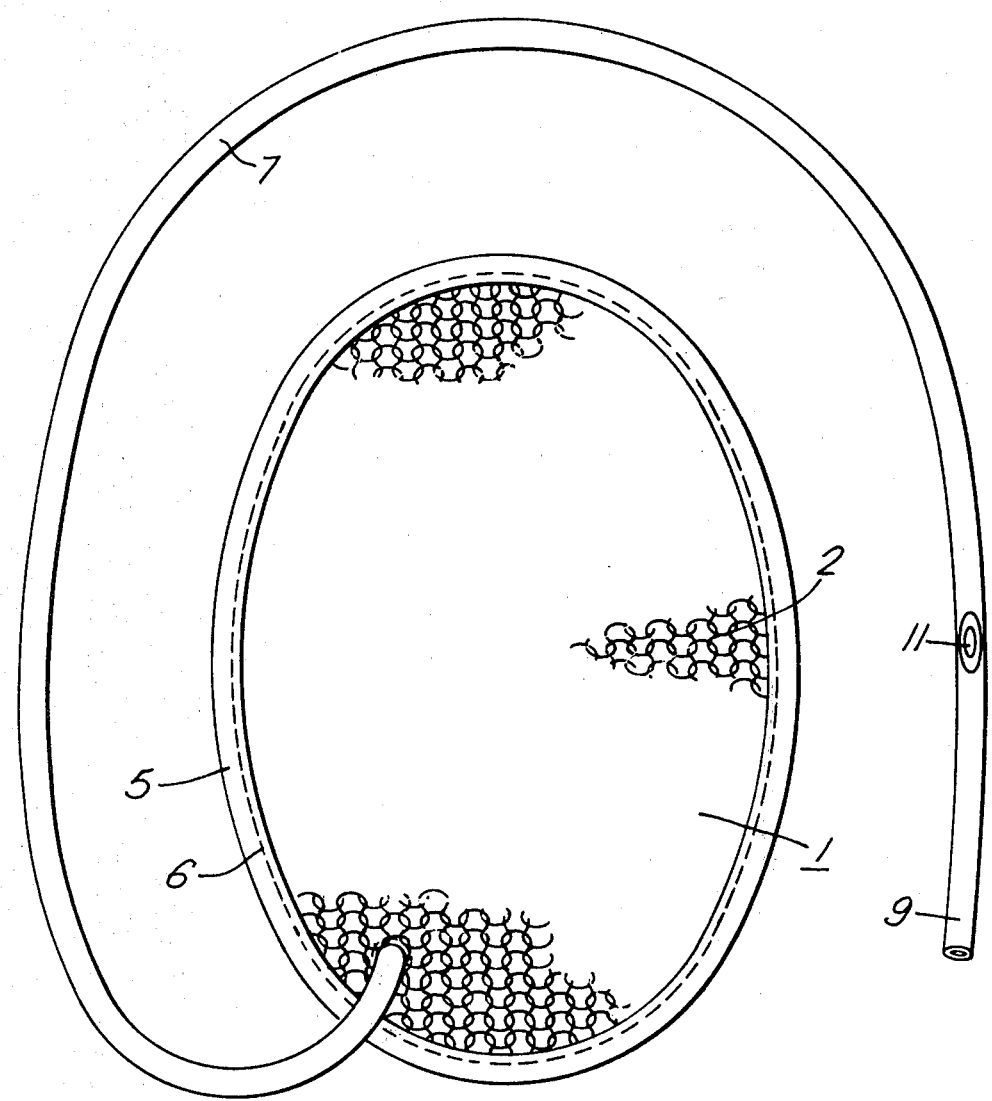
FIG. 1 is a plan view of a cardiac cushion.

The cardiac cushion 1 shown in FIGS. 1 to 4 comprises two layers of a knitted plastics white-spun-nylon filament mesh 2, a layer or pad 3 of non-woven cotton-fabric, and a lint-free nylon layer or backing 4. The mesh layer 2, pad 3 and backing 4 are held together around their peripheries by cotton tape 5 which is doubled over along its length and held by stitching 6, the pad 3 being sandwiched between the layers of nylon mesh 2 and the nylon backing 4. The cushion 1 is oval shaped, being about 95 mm across its minor axis and about 135 mm across its major axis.

Figure 2:
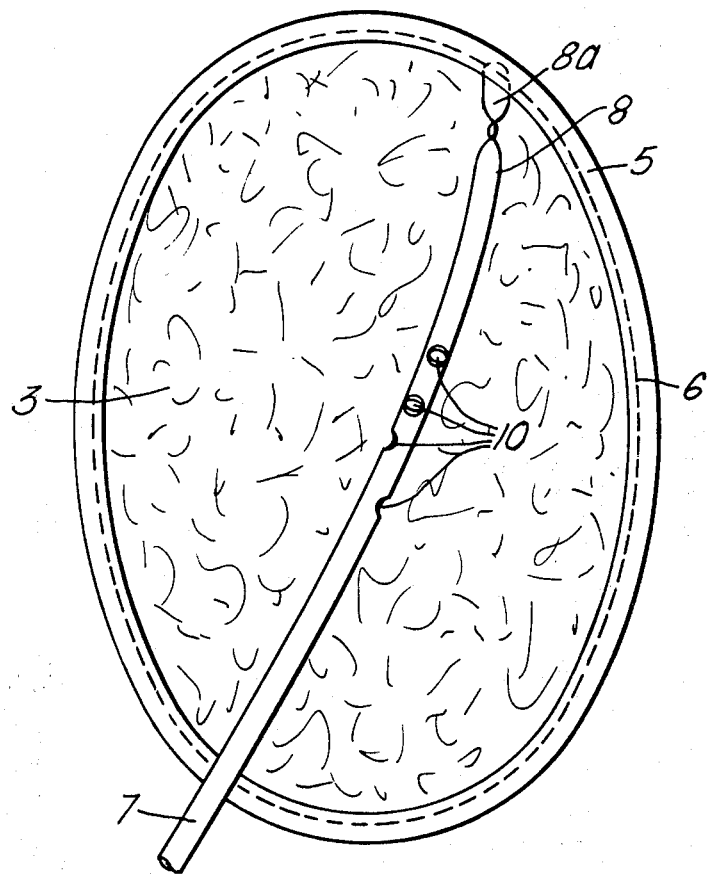
FIG. 2 is a plan view of the cardiac cushion with parts thereof removed to reveal other features of the cushion.
Figure 3:
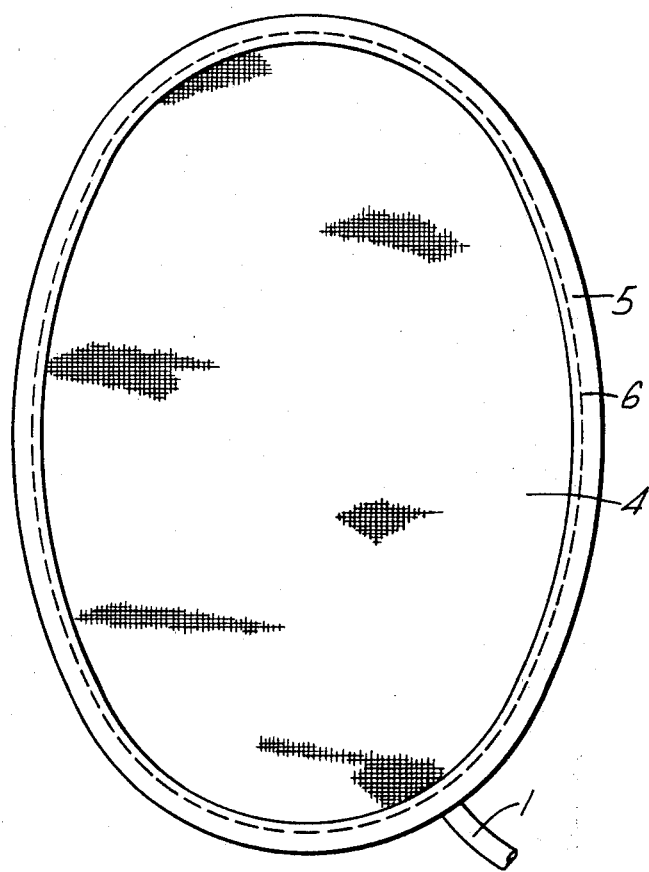
FIG. 3 is an underneath view of the cushion.
Figure 4:
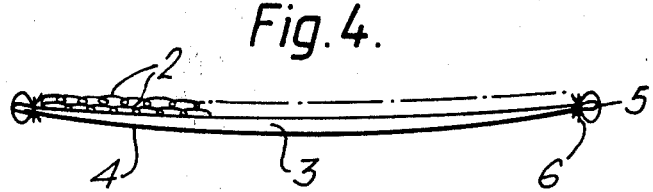
FIG. 4 is a sectional elevational view of the cushion.

The proximal end 8 of a flexible PVC tube 7 extends underneath the two layers of mesh 2, the tube entering the cushion at a point near the periphery of the cushion. The flexible PVC tube 7 is closed at its proximal end 8 by heat sealing, during which process a thin portion 8a of the PVC material is drawn out from that end. This thin portion 8a is held in place by the stitching 6 at the periphery of the cushion at a point furthest from the point where the tube enters the cushion. The thin portion 8a is twisted so that the end 8 is held more firmly in place. Holes 10 cut into the tube 7 near the end 8 are located underneath the nylon mesh layers 2 to assist drainage of fluid from the cushion. The proximal end 8 of the tube 6 can be seen more clearly in FIG. 2, in which the mesh layers 2 have been removed for this purpose. Four holes 10 are shown in FIG. 2, but there could be more holes or fewer holes, so long as there is at least one.

The tube 7 extends through the nylon mesh layers 2 away from the cushion 1. Near to the distal end 9 of the tube 7, a shallow slice has been cut to leave an aperture 11 that is easily blocked by a finger or thumb.

Figure 5:
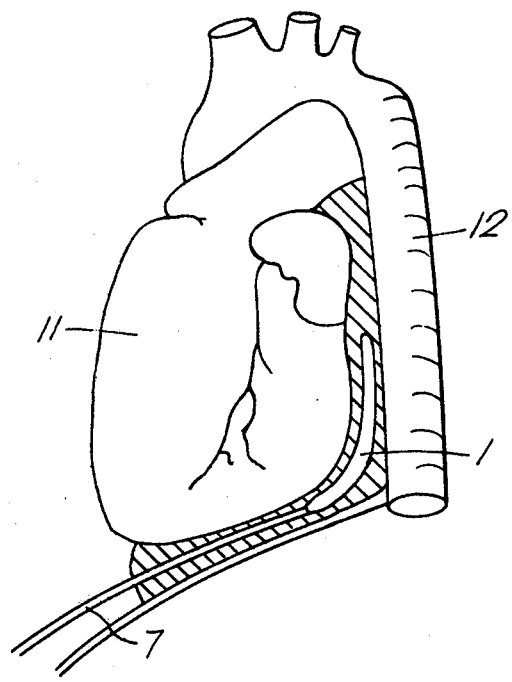
FIGS. 5 and 6 show side and underneath views of a heart with the cardiac cushion in position ready for use.
Figure 6:
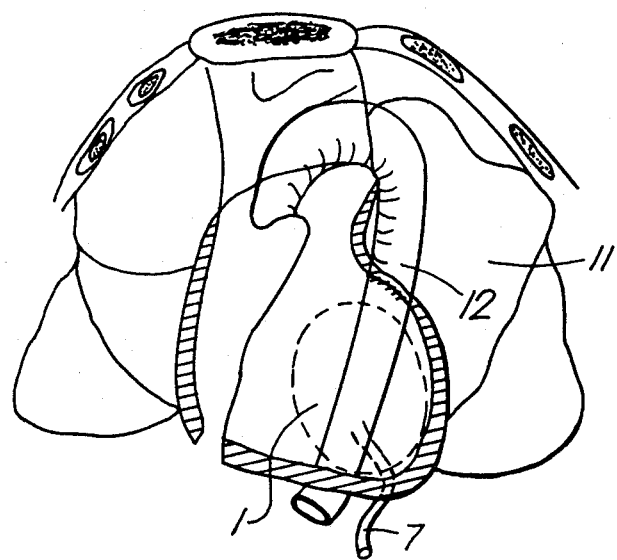

When the cushion 1 is in use, it is positioned between the heart 11 and the descending thoracic aorta 12 as shown in FIGS. 5 and 6. The fact that the cushion 1 is flexible makes is much easier to manipulate and locate behind the heart, thus reducing the time taken for the operation, increasing the efficiency of the operation as a whole, and decreasing the risk of myocardial damage. The distal end 9 of the PVC tube 7 is connected to a suction pump (not shown). A cold saline solution or slush is directed onto the heart to flow over and around it. The suction pump will normally be drawing air through the aperture 11. However, when excess solution or slush has accumulated around the heart, the aperture 11 is covered by a finger or thumb. This blocks the passage of air through it to cause the suction pump to draw the excess solution away from the heart via the holes 10 near the proximal end 8 inside the cushion 1.

The two layers 2 of nylon filament mesh 2 naturally stand proud of the cushion ensuring adequate spacing between the heart and the aorta for circulation of cooling fluid in that region. The thermally insulating properties of the materials of which the cushion is made further enhance the thermal insulation between heart and aorta, reducing the risk of a "hot spot" in the posterior pericardium.

The filamentous nature of the top two layers 2 of the cushion 1 ensure that the cold saline solution or slush can flow into and out of the cushion. Because the non-woven cotton-fabric pad 3 is absorbent, there will always be an adequate quantity of coolant between the heart and aorta. The nylon backing 4, being lint-free, will not leave any filaments behind on the human tissue it comes into contact with.

The inexpensive materials used for the manufacture of the cushion allow it to be used once and then disposed of. This eliminates the risk of transfer to tissue, especially proteins, from one patient to another.

The dimensions already given for the cushion are acceptable for many adults. A smaller size for adults would be about 120 mm (major axis) by about 75 mm (minor axis) for adults. A paediatric size would be about 80 mm by 50 mm, and a size for infants about 65 mm by 40 mm.

The cardiac cushion described is sterilisable by autoclave, irradiation or E.T.O., and is suitable for all valve procedures, fallots, and V.S.D's.

Instead of P.V.C., the tube 6 could be made of silicone rubber.

We claim:

1. A surgical cushion comprising a layer of flexible, open-form knitted plastics filament mesh, a further layer of flexible material secure with the first-mentioned layer, a flexible tube, a proximal end portion of said flexible tube which is secure with and extends between said two layers, and at least one hole-defining part of said tube defining a hole of the tube at a position between said layers, whereby cooling fluid in regions within and near to the cushion when it is in use may be drawn off.

2. A surgical cushion according to claim 1, wherein the mesh comprises spun-nylon.

3. A surgical cushion comprising a layer of flexible, open-form material, a layer of flexible lint-free nylon backing secure with the first-mentioned layer, a flexible tube, a proximal end portion of said flexible tube which is secure with and extends between said two layers, and at least one hole-defining part of said tube defining a hole of the tube at a position between said layers, whereby cooling fluid in regions within and near to the cusion when it is in use may be drawn off.

4. A surgical cushion according to claim 3, wherein the first-mentioned layer comprises a knitted plastics filament mesh.

5. A surgical cushion according to claim 4, wherein the mesh comprises spun-nylon.

6. A surgical cushion comprising a layer of flexible, open-form knitted plastics filament mesh, a layer of flexible lint-free free nylon backing secure with the first-mentioned layer, a flexible tube, a proximal end portion of said flexible tube which is secure with and extends between said two layers, and at least one hole-defining part of said tube defining a hole of the tube at a position between said layers, whereby cooling fluid in regions within and nearto the cushion when it is in use may be drawn off.

7. A surgical cushion according to claim 6, wherein the mesh comprises spun-nylon.

8. A surgical cushion comprising a layer of flexible, open-form knitted spun-nylon filament mesh, a flexible lint-free nylon backing layer secure with the first-mentioned layer, a flexible tube, a proximal end portion of said flexible tube which is secure with and extends between said two layers, and at least one hole-defining part of said tube defining a hole of the tube at a position between said layers, whereby cooling fluid in regions within and nearto the cushion when it is in use may be drawn off.

* * * * *